United States Patent [19]
Papay

[11] Patent Number: 5,866,106
[45] Date of Patent: Feb. 2, 1999

[54] VITAMIN/MINERAL-ENRICHED CYANOACRYLATE COSMETIC

[75] Inventor: Kristy L. Papay, Orange, Calif.

[73] Assignee: Pacer Technology, Rancho Cucamonga, Calif.

[21] Appl. No.: 794,123

[22] Filed: Feb. 3, 1997

[51] Int. Cl.[6] .............................. A61K 6/00; A61K 7/00; A61K 7/04
[52] U.S. Cl. .............................. 424/61; 424/401
[58] Field of Search ........................ 424/61, 401; 132/73; 156/133.9

[56] References Cited

U.S. PATENT DOCUMENTS

| | | | |
|---|---|---|---|
| 3,887,702 | 6/1975 | Baldwin | 424/61 |
| 4,363,796 | 12/1982 | Bouillon et al. | 424/61 |
| 4,844,102 | 7/1989 | Repensek et al. | 132/73 |
| 4,919,920 | 4/1990 | Devos | 424/61 |
| 5,206,011 | 4/1993 | Pappas et al. | 424/61 |
| 5,210,133 | 5/1993 | O'Lenick, Jr. | 525/54.1 |
| 5,484,586 | 1/1996 | Bedard | 424/61 |
| 5,632,973 | 5/1997 | Keller | 424/61 |

*Primary Examiner*—Thurman K. Page
*Assistant Examiner*—Sharon Howard
*Attorney, Agent, or Firm*—Thomas E. Schatzel; Law Offices of Thomas E. Schatzel, A Prof. Corporation

[57] ABSTRACT

A nail tip adhesive is made by the process of mixing cyanoacrylate and a vitamin fortifier in a proportion by weight in the range of 0.0001% to 0.1% vitamin-to-cyanoacrylate, wherein the shelf life of the cyanoacrylate is at least not substantially shortened by adding such vitamin. Such vitamin fortifier comprises at least one of vitamin A, vitamin D-3, vitamin E, vitamin K, vitamin B-1, vitamin B-2, vitamin B-6, vitamin B-12, vitamin C, niacinamide, folic acid, panthothenic acid, and biotin.

16 Claims, 2 Drawing Sheets

VITAMIN/MINERAL-ENRICHED CYANOACRYLATE COSMETIC

BACKGROUND OF THE INVENTION

1. Field of the Invention

The invention relates generally to cosmetics and adhesives, and more particularly to adhesive compounds that include vitamins, minerals, and other lotions and nutrients generally regarded as beneficial to humans.

2. Description of the Prior Art

Cyanoacrylates, or more specifically ethyl a cyanoacrylates, are variously referred to as EACA, Instant Magic, Krazy Glue, Miracle Glue, Nail Glue, Super Glue, etc. Such are conventionally used for adhesives, aircraft and automobile industry, cosmetics (nail mending kits), electronic industry (circuit boards), leather finish resins, medicine (binding of tissue, sealing of wounds, ileostomy appliances), meat slaughter (carcass sealing), paint vehicles (water emulsion), paper and textile coatings, perfume, rubber, and textile and paper coatings.

Vitamins play varied roles in preventing certain diseases, such as cancer. Small quantities can be sufficient to maintain a good health. An adequate intake of minerals is also essential to remain healthy. More than sixty different minerals contribute to the overall health of the human body. Among them, twenty-two are considered to be essential. Minerals, and many trace elements have been recently proposed as miracle solutions to health problems created by modern life. External sources of vitamins and minerals are required, because our bodies do not produce all that are required. The most common source is the food we take in.

A well balanced diet means eating vegetables and fruits, whole grain cereals, meat or fish or substitute, and milk products, in balanced proportions each day. But people are often in a hurry, skip meals or run to the restaurant at lunch time. Many think that a bottle of multi-vitamins can compensate for bad eating habits. However, vitamins typically work only in combination with food. The pure vitamins and minerals are not a substitute for poor eating habits.

The thirteen essential vitamins are divided between two large groups. Vitamins A, D, E and K are accumulated in the liver and in the adipose tissue (fat). Such vitamins are not easily eliminated, and problems can develop if taken in quantities that are excessive. Complex B vitamins, e.g., thiamin, riboflavin, niacin, panthothenic acid or B5, pyridoxine or B6, biotin, folic acid and B12, and vitamin C, are all soluble in water. Such vitamins can be retained in proper concentrations by the body because any excess detected can be eliminated quickly in urine.

A few well-intentioned people have a tendency to overdose with vitamins A, C and E, because such vitamins have the false reputation of curing or preventing almost everything, e.g., vitamin A for curing cancer, improving eyesight and making the skin look younger. Vitamin E is reputed to prevent heart conditions, improve sexual performance and even to postpone aging. Vitamin C is attributed many virtues, from the prevention of colds to the cure of cancer. But a vitamin surplus cannot be expected to improve the performance of an organ that is already functioning well. Overdoses of vitamins A, D or E may actually be harmful since they have a tendency to accumulate in the body.

Many vitamin and mineral supplements often contain more quantity than is necessary for a healthy diet. The so-called "natural" vitamins are not better nor better absorbed than the others or the ones found in food. Cautions have been issued about taking an excess of mineral supplements, it is not known yet what daily quantities mark the dividing line between benefit and harm.

Pregnant women have an increased need for calcium and vitamin D, and milk is generally regarded as a good source. Folic acid and iron supplement are also commonly supplemented. Older people who under-eat often need to take multivitamins, or risk suffering a zinc deficiency. People who drink alcohol to excess often have an unbalanced diet and suffer from a lack of group B vitamins. Smokers need more vitamin C, and a glass of orange juice once a day is usually sufficient. In general, North Americans eat too much salt but not enough calcium, iron and zinc. Women have a higher risk of lacking calcium and iron.

The list of vitamins commonly included in supplements includes vitamin A, D-3, E, K, B-1, B-2, B-6, B-12, C, niacinamide, folic acid, panthothenic acid, and biotin. Associated nutritional factors that can be added include bioflavonoids, rutin, hesperidin, choline, inositol, PABA.

Common minerals to include are calcium, magnesium, manganese, copper, zinc, iodine, selenium, chromium, molybdenum, and vanadium. Such trace minerals are every bit as important in nutrition as vitamins. Chromium supports the pancreas in its production of insulin, and controls carbohydrate metabolism. Since children have a tendency to eat far too much sugar and other refined carbohydrates, chromium is an important ingredient in any children's supplement. Selenium, molybdenum and vanadium are antioxidants that help fight the free radicals formed because of various pollutants. Such free radicals are suspected of actually stimulating the formation of cancer.

Moisturizers are needed for the conditioning and growth of healthy nail beds. But such moisturizers included in fingernail cosmetic adhesives and polishes are unknown in the prior art.

Cyanoacrylates, in general, have delicate chemistries that can be easily activated to cure. Therefore, additives and fillers cannot be simply mixed in without regard to their contributions to the complex chemistries involved and the effect the mixture will have on activating the cyanoacrylate cure. Shelf life of one year or more are desirable and any additives included should not decrease the expected shelf life that consumers have grown accustomed to.

SUMMARY OF THE PRESENT INVENTION

It is therefore an object of the present invention to provide a fingernail cosmetic based on cyanoacrylate with minerals, vitamins and moisturizers.

It is another object of the present invention to provide cyanoacrylate compounds that are enriched with minerals, vitamins and moisturizers which have long shelf lives.

Briefly, a nail tip adhesive embodiment of the present invention includes cyanoacrylate combined with at least one of a nutritional vitamin and mineral in a proportion in the range of 0.0001% to 0.1% by weight. The additives are individually limited to prevent unintended activation of the cure and to promote long product shelf life.

An advantage of the present invention is that when added to a conventional nail polish, a nail coating is provided that has an increased affinity to fingernails and therefore resists chipping and flaking.

These and other objects and advantages of the present invention will no doubt become obvious to those of ordinary skill in the art after having read the following detailed description of the preferred embodiments which are illustrated in the various drawing figures.

IN THE DRAWINGS

DETAILED DESCRIPTION OF THE PREFERRED EMBODIMENTS

Figure 1:
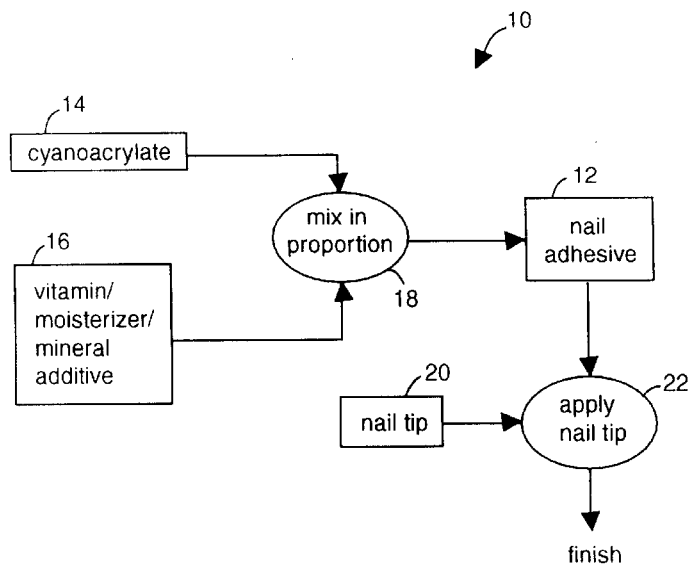
FIG. 1 is a process diagram illustrating the making of a nail tip adhesive product of the present invention.

FIG. 1 illustrates a process 10 for making a nail tip adhesive product 12 which is an embodiment of the present invention. A cyanoacrylate 14 is mixed in a step 18 with a vitamin-moisturizer-mineral additive 16 comprising at least one of: vitamins A, D-3, E, K, B-1, B-2, B-6, B-12, C; niacinamide; folic acid; panthothenic acid; biotin; bioflavonoids; rutin; hesperidin; choline; inositol; PABA; lanolin; aloe; calcium salt of pantophenic acid or any other calcium salt hydrate; iron; magnesium; manganese; copper; zinc; iodine; selenium; chromium; molybdenum; and vanadium. The proportion, by weight, of vitamin/mineral additive 16 to the cyanoacrylate 14 is in the range of 0.0001% to 0.1%. The upper limit is constrained by the particular chemistry of each constituent in the additive to cause activation of the cure of the cyanoacrylate 14. Such proportions of constituents are critically and independently limited to amounts that do not effect, or do not significantly reduce, the shelf life of the cyanoacrylate 14. A nail tip 20 is applied in a step 22 to a fingernail with the nail adhesive 12.

Figure 2:
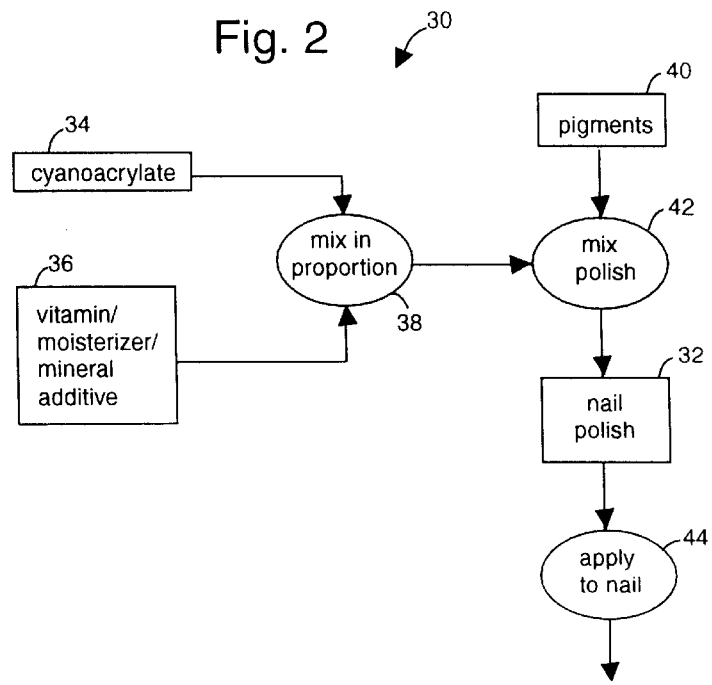
FIG. 2 is a process diagram illustrating the making of a nail polish product of the present invention.

FIG. 2 illustrates a process 30 for making a nail polish product 32 which is an embodiment of the present invention. A cyanoacrylate 34 is mixed in a step 38 with a vitamin-moisturizer-mineral additive 36 comprising at least one of: vitamins A, D-3, E, K, B-1, B-2, B-6, B-12, C; niacinamide; folic acid; panthothenic acid; biotin; bioflavonoids; rutin; hesperidin; choline; inositol; PABA; lanolin; aloe; calcium salt hydrate; iron; magnesium; manganese; copper; zinc; iodine; selenium; chromium; molybdenum; and vanadium. The proportion, by weight, of vitamin/mineral additive 36 to the cyanoacrylate 34 is in the range of 0.0001% to 0.1%. The upper limit is constrained by the particular chemistry of each constituent in the additive to cause activation of the cure of the cyanoacrylate 34. Such proportions of constituents are critically and independently limited to amounts that do not effect, or do not significantly reduce, the shelf life of the cyanoacrylate 34. A pigment 40 is mixed in a step 42 to produce the nail polish 32. Such nail polish 32 is applied to a fingernail in a step 44.

Figure 3:
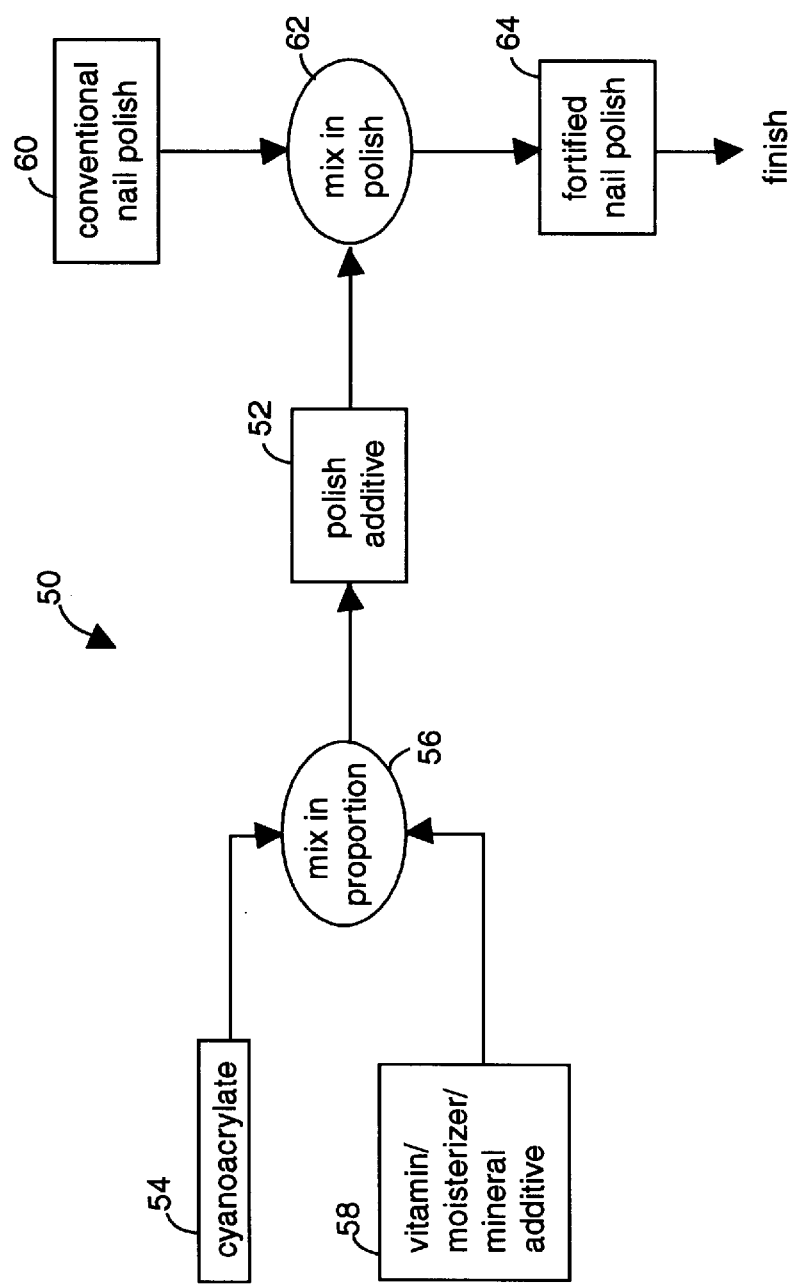
FIG. 3 is a process diagram illustrating the making of a nail polish additive of the present invention.

FIG. 3 illustrates a process 50 for making a nail polish additive 52 which is an embodiment of the present invention. A cyanoacrylate 54 is mixed in a step 56 with a vitamin-moisturizer-mineral additive 58 comprising at least one of: vitamins A, D-3, E, K, B-1, B-2, B-6, B-12, C; niacinamide; folic acid; panthothenic acid; biotin; bioflavonoids; rutin; hesperidin; choline; inositol; PABA; lanolin; aloe; calcium salt hydrate; iron; magnesium; manganese; copper; zinc; iodine; selenium; chromium; molybdenum; and vanadium. The proportion, by weight, of vitamin/mineral additive 58 to the cyanoacrylate 54 is in the range of 0.0001% to 0.1%. The upper limit is constrained by the particular chemistry of each constituent in the additive to cause activation of the cure of the cyanoacrylate 54. Such interactions are easily and readily discernible to artisans. Such proportions of constituents are critically and independently limited to amounts that do not effect, or do not significantly reduce, the shelf life of the cyanoacrylate 54. A conventional nail polish 60 is mixed in a step 62 to produce a fortified nail polish 64. Such nail polish 64 can be applied to a fingernail at any time during the shelf life.

Although the present invention has been described in terms of the presently preferred embodiments, it is to be understood that the disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. A nail tip adhesive made by the process of:
  mixing cyanoacrylate and a vitamin in a proportion by weight in the range of 0.0001% to 0.1% vitamin-to-cyanoacrylate, wherein the shelf life of the cyanoacrylate is at least not substantially shortened by adding such vitamin;
  wherein, such proportions of constituents are critically and independently limited to amounts that do not effect, or do not significantly reduce, the shelf life of the cyanoacrylate.

2. The nail adhesive of claim 1, wherein:
  said vitamin comprises at least one of vitamin A, vitamin D-3, vitamin E, vitamin K, vitamin B-1, vitamin B-2, vitamin B-6, vitamin B-12, vitamin C, niacinamide, folic acid, panthothenic acid, and biotin.

3. A nail tip adhesive made by the process of:
  mixing cyanoacrylate and a moisturizer in a proportion by weight in the range of 0.0001% to 0.1% moisturizer-to-cyanoacrylate, wherein the shelf life of the cyanoacrylate is at least not substantially shortened by adding such moisturizer;
  wherein, such proportions of constituents are critically and independently limited to amounts that do not effect, or do not significantly reduce, the shelf life of the cyanoacrylate.

4. The nail adhesive of claim 3, wherein:
  said moisturizer comprises at least one of aloe or lanolin.

5. A nail tip adhesive made by the process of:
  mixing cyanoacrylate and a mineral in a proportion by weight in the range of 0.0001% to 0.1% mineral-to-cyanoacrylate, wherein the shelf life of the cyanoacrylate is at least not substantially shortened by adding such mineral;
  wherein, such proportions of constituents are critically and independently limited to amounts that do not effect, or do not significantly reduce, the shelf life of the cyanoacrylate.

6. The nail adhesive of claim 5, wherein:
  said mineral comprises at least one of calcium salt hydrate, iron, magnesium, manganese, copper, zinc, iodine, selenium, chromium, molybdenum, and vanadium.

7. A nail tip adhesive made by the process of:
  mixing cyanoacrylate and a vitamin-moisturizer-mineral additive in a proportion by weight in the range of 0.0001% to 0.1% vitamin-moisturizer-mineral-additive to cyanoacrylate, wherein the shelf life of the cyanoacrylate is at least not substantially shortened by adding such vitamin-moisturizer-mineral additive;
  wherein, such proportions of constituents are critically and independently limited to amounts that do not effect, or do not significantly reduce, the shelf life of the cyanoacrylate.

8. The nail adhesive of claim 7, wherein:

said vitamin-moisturizer-mineral additive comprises at least two of vitamin A, vitamin D-3, vitamin E, vitamin K, vitamin B-1, vitamin B-2, vitamin B-6, vitamin B-12, vitamin C, niacinamide, folic acid, panthothenic acid, biotin, aloe, lanolin, calcium salt hydrate, iron, magnesium, manganese, copper, zinc, iodine, selenium, chromium, molybdenum, and vanadium.

9. A nail polish made by the process of:

mixing cyanoacrylate and a vitamin in a proportion by weight in the range of 0.0001% to 0.1% vitamin-to-cyanoacrylate, wherein the shelf life of the cyanoacrylate is at least not substantially shortened by adding such vitamin; and mixing a pigment with said mixture of cyanoacrylate and vitamin for application as a fortified cosmetic to a fingernail;

wherein, such proportions of constituents are critically and independently limited to amounts that do not effect, or do not significantly reduce, the shelf life of the cyanoacrylate.

10. The nail polish of claim 9, w herein:

said vitamin comprises a t least one of vitamin A, vitamin D-3, vitamin E, vitamin K, vitamin B-1, vitamin B-2, vitamin B-6, vitamin B-12, vitamin C, niacinamide, folic acid, panthothenic acid, and biotin.

11. A nail polish made by the process of:

mixing cyanoacrylate and a moisturizer in a proportion by weight in the range of 0.0001% to 0.1% moisturizer-to-cyanoacrylate, wherein the shelf life of the cyanoacrylate is at least not substantially shortened by adding such moisturizer; and mixing a pigment with said mixture of cyanoacrylate and moisturizer for application as a fortified cosmetic to a fingernail;

wherein, such proportions of constituents are critically and independently limited to amounts that do not effect, or do not significantly reduce, the shelf life of the cyanoacrylate.

12. The nail polish of claim 11, wherein:

said moisturizer comprises at least one of aloe or lanolin.

13. A nail polish made by the process of:

mixing cyanoacrylate and a mineral in a proportion by weight in the range of 0.0001% to 0.1% mineral-to-cyanoacrylate, wherein the shelf life of the cyanoacrylate is at least not substantially shortened by adding such mineral; and mixing a pigment with said mixture of cyanoacrylate and mineral for application as a fortified cosmetic to a fingernail;

wherein, such proportions of constituents are critically and independently limited to amounts that do not effect, or do not significantly reduce, the shelf life of the cyanoacrylate.

14. The nail polish of claim 13, wherein:

said mineral comprises at least one of calcium salt hydrate, iron, magnesium, manganese, copper, zinc, iodine, selenium, chromium, molybdenum, and vanadium.

15. A nail polish made by the process of:

mixing cyanoacrylate and a vitamin-moisturizer-mineral additive in a proportion by weight in the range of 0.0001% to 0.1% vitamin-moisturizer-mineral-additive to cyanoacrylate, wherein the shelf life of the cyanoacrylate is at least not substantially shortened by adding such vitamin-moisturizer-mineral additive; and mixing a pigment with said mixture of cyanoacrylate and vitamin-moisturizer-mineral additive for application as a fortified cosmetic to a fingernail;

wherein, such proportions of constituents are critically and independently limited to amounts that do not effect, or do not significantly reduce, the shelf life of the cyanoacrylate.

16. The nail polish of claim 15, wherein:

said vitamin-moisturizer-mineral additive comprises at least two of vitamin A, vitamin D-3, vitamin E, vitamin K, vitamin B-1, vitamin B-2, vitamin B-6, vitamin B-12, vitamin C, niacinamide, folic acid, panthothenic acid, biotin, aloe, lanolin, calcium salt hydrate, iron, magnesium, manganese, copper, zinc, iodine, selenium, chromium, molybdenum, and vanadium.

* * * * *